US012611446B2

(12) United States Patent
Owen

(10) Patent No.: US 12,611,446 B2
(45) Date of Patent: Apr. 28, 2026

(54) CANNABINOID PRODUCT FOR IMPROVING MUSCULOSKELETAL HEALTH

(71) Applicant: Lonza Greenwood LLC, Greenwood, SC (US)

(72) Inventor: Kevin Owen, Canyon, TX (US)

(73) Assignee: Lonza Greenwood LLC, Greenwood, SC (US)

( * ) Notice: Subject to any disclaimer, the term of this patent is extended or adjusted under 35 U.S.C. 154(b) by 1063 days.

(21) Appl. No.: 17/761,664

(22) PCT Filed: Sep. 30, 2020

(86) PCT No.: PCT/US2020/053565
§ 371 (c)(1),
(2) Date: Mar. 18, 2022

(87) PCT Pub. No.: WO2021/067452
PCT Pub. Date: Apr. 8, 2021

(65) Prior Publication Data

US 2022/0331406 A1 Oct. 20, 2022

Related U.S. Application Data

(60) Provisional application No. 62/908,141, filed on Sep. 30, 2019.

(51) Int. Cl.

| | |
|---|---|
| ***A23L 33/105*** | (2016.01) |
| ***A23K 10/20*** | (2016.01) |
| ***A23K 10/30*** | (2016.01) |
| ***A23K 20/121*** | (2016.01) |
| ***A23K 20/147*** | (2016.01) |
| ***A23K 50/40*** | (2016.01) |
| ***A23L 33/17*** | (2016.01) |
| ***A23L 33/18*** | (2016.01) |
| ***A61K 9/00*** | (2006.01) |
| ***A61K 31/00*** | (2006.01) |
| ***A61K 31/60*** | (2006.01) |
| ***A61K 38/39*** | (2006.01) |
| ***A61P 19/02*** | (2006.01) |

(52) U.S. Cl.
CPC .............. *A61K 38/39* (2013.01); *A23K 10/30* (2016.05); *A23K 20/147* (2016.05); *A23K 50/40* (2016.05); *A23L 33/105* (2016.08); *A23L 33/18* (2016.08); *A61K 9/0056* (2013.01); *A61K 31/60* (2013.01); *A61K 31/658* (2023.05); *A61P 19/02* (2018.01)

(58) Field of Classification Search
CPC ...... A61K 38/39; A61K 31/658; A61K 31/05; A61K 31/192; A61K 31/352; A23K 10/30; A61P 19/02
See application file for complete search history.

(56) References Cited

U.S. PATENT DOCUMENTS

| | | | |
|---|---|---|---|
| 2015/0119335 A1 | 4/2015 | Dijkstra et al. |
| 2016/0361290 A1 | 12/2016 | Robson et al. |
| 2018/0280464 A1 | 10/2018 | Martin |
| 2020/0069776 A1 | 3/2020 | Skodda |

FOREIGN PATENT DOCUMENTS

| | | | |
|---|---|---|---|
| WO | WO-2017066474 A1 * | 4/2017 | ........... A61K 36/324 |
| WO | WO2020168073 | 8/2020 | |

OTHER PUBLICATIONS

Formulation definition, accessed Sep. 3, 2025 at URL vocabulary.com/dictionary/formulation, 1 page, (2015)) (Year: 2015).*
Database GNPD [Online] MINTEL; Aug. 20, 2019, anonymous: 11GI ow Bi oCe 11 Collagen + PABA Silica + Full Spectrum Hemp Extract 11, Database accession No. 6758899 p. 4.
Holly T. Philpott et al: "Attenuation of early phase inflarrmation by cannabidiol prevents pain and nerve damage in rat osteoarthritis :", PAIN, vol. 158, No. 12, Dec. 1, 2017, pp. 2442-2451.
International Search Report and Written Opinion for PCT/US2020/053565 dated Dec. 22, 2020, 16 pages.
Amandean, CBD & Collagen is The New Bulletproof Coffee, published Apr. 18, 2019.

* cited by examiner

*Primary Examiner* — Julie Ha
*Assistant Examiner* — Kristina M Hellman
(74) *Attorney, Agent, or Firm* — Dority & Manning, P.A.

(57) ABSTRACT

The present disclosure is directed to a composition or nutritional product containing a cannabinoid in combination with an adjuvant, such as a Type II collagen. The different nutraceutical agents are capable of synergistically working together to improve the health and well-being of a human or animal. For instance, the nutritional product can be used in many different applications, such as to treat joint discomfort and pain, and/or to improve muscular health.

8 Claims, No Drawings

CANNABINOID PRODUCT FOR IMPROVING MUSCULOSKELETAL HEALTH

RELATED APPLICATIONS

The present application is based on and claims priority to U.S. Provisional Patent application Ser. No. 62/908,141, filed on Sep. 30, 2019, which is incorporated herein by reference.

BACKGROUND

Cannabis, or the cannabis plant, may refer to both marijuana, which is generally used for recreational purposes, and hemp, which is generally used in industrial applications. Cannabis is a green and/or brown mixture of dried, shredded leaves, stems, stalks, seeds and flowers of the plant, and may reference leaves, stems, seeds, and flowers from a Cannabis plant, varieties of which include *Cannabis sativa* or *Cannabis indica*. Hemp (and particularly the industrial hemp variety), have a very similar appearance to marijuana, but unlike the cannabis plant variety referred to by marijuana, hemp generally only contains low amounts of tetrahydrocannabinol (THC), whereas both hemp and marijuana can include high amounts of cannabidiol (CBD). For instance, hemp, and particularly industrial hemp may contain less than about 0.3% THC whereas the cannabis variety referred to by marijuana may contain anywhere from 5% to 30% THC. Recently, over 25 states in the United States have legalized the use of cannabis for at least medical purposes. In addition, Canada has now legalized the use of cannabis for medical and recreational use. In view of these recent developments, the commercialization of cannabis has dramatically increased.

Cannabis, for instance, is becoming a more and more popular drug for pain relief in lieu of conventional pain relief medicines, such as opioids. Opioids are powerful pain relief medications that relieve pain by acting on the nervous system. They are typically used to treat severe pain after surgery and are also used to treat chronic pain, such as joint pain. Unfortunately, however, opioids come with many risks. For example, opioids are highly addictive which has led to an epidemic of drug misuse.

In view of the above drawbacks, more and more people in the medical community have begun to view cannabis as a legitimate alternative to the use of opioids for pain relief. For instance, THC acts on specific receptors in the brain which lead to a feeling of euphoria and a relaxed state. The highest concentrations of THC in cannabis are found in the dried flowers or buds. Cannabis is typically regulated based upon the amount of THC found in the material.

Although CBD does interact with pain receptors in the brain, CBD does not create the same euphoric feeling caused by THC. CBD, however, exerts pain-relieving and anti-inflammatory effects. Cannabis, and especially CBD, do not have the same addictive effect as many opioids.

CBD can be administered in a variety of forms. For example, it can be delivered in the form of an oil, a powder, or as nanoparticles, which are more quickly absorbed by the body.

Due to the potential of cannabis to be used as a therapeutic substance with low risk for addiction, there is a need to maximize the benefits of cannabis and extend its use into new applications.

SUMMARY

The present disclosure concerns a composition or nutritional product that includes a cannabinoid administered to a mammal, a patient, or a healthy individual to promote or improve musculoskeletal health. The composition further comprises a collagen source, such as a Type II collagen source. It is believed that the cannabinoid of the present disclosure not only provides pain relief but can also synergistically work in conjunction with the collagen source for promoting or modulating the health of the mammal, such as joint health.

The collagen source incorporated into the nutritional product of the present disclosure can vary. For instance, it may be a Type II collagen source comprising undenatured, denatured, or hydrolyzed Type II collagen. In an alternative embodiment, the collagen source can be a bioactive peptide derived from Type II collagen.

The nutritional product of the present disclosure can be used to treat all different types of musculoskeletal ailments in mammals, which are due to a disease, age (including arthritis), or various normal strenuous activities (e.g., running, walking, stair climbing, exercising, etc.), in animals or humans. The method includes administering to the mammal a therapeutically effective amount of a cannabinoid in combination with a collagen source. The compositions or products, which can be in the form of oral dosage vessels, can be administered to the mammal in an amount sufficient to reduce joint discomfort or pain, or to begin and support the healing process, or any combination thereof. Additionally, the compositions and products can be used to maintain musculoskeletal health such as healthy bones and joints for mammals of any age. Further, the compositions and products can be used as a prenatal and/or multivitamin/mineral supplement.

The cannabinoid may be any known cannabinoid. In one embodiment, the cannabinoid is selected from the group consisting of cannabidiolic acid (CDBA), tetrahydrocannabinolic acid (THCA), cannabidiol (CBD), tetrahydrocannabinol (THC), cannabinol (CBN), cannabigerol (CBG), and cannabidivarin (CBDv), cannabichromene (CBC), tetrahydrocannabivarin (THCv), Δ-8-tetrahydrocannabinol (Δ-8-THC), or any combination thereof, including their components, derivatives, and metabolites. The cannabinoid may be obtained from a plant source or be may be obtained as a product of fermentation. If the cannabinoid is obtained through fermentation, the cannabinoid may be a type present in only small amounts in plants or a type that is difficult to extract from plants. The cannabinoid may be present in the form of an oil, powder, or as a nanoparticulate material. Additionally, the cannabinoid may be delivered using spray-dried dispersion or micronization technology. Such technologies may be utilized to enhance the bioavailability of the cannabinoid.

The collagen source and the cannabinoid can be combined together and administered to the mammal. Alternatively, the collagen source and the cannabinoid can be administered separately to the mammal. In one aspect, the collagen source and the cannabinoid are administered orally to the mammal. For example, the collagen source and the cannabinoid can be contained in a food composition or beverage. Additionally, in one embodiment, the food composition is a pet food for administering the collagen source and the cannabinoid to an animal.

The amount of the collagen source and the amount of the cannabinoid administered to the mammal can vary depending upon various factors including the type of mammal being treated, the ailment being treated, and the weight or mass of the mammal. For instance, the collagen source can be administered to the mammal in an amount of from about 1 μg/kg body weight/day to about 1 g/kg body weight/day, such as from about 250 μg/kg body weight/day to about 1 mg/kg body weight/day. The amount of collagen administered to the mammal may be on the low end of the dosage range when delivered as a nanoparticle. The cannabinoid can be administered to the mammal generally in an amount from about 1 μg/kg body weight/day to about 600 mg/kg body weight/day, such as in an amount from about 1 mg/kg body weight/day to about 20 mg/kg body weight/day. The amount of cannabinoid administered to the mammal may be on the low end of the dosage range when delivered as a nanoparticle. The collagen source and/or the cannabinoid can be administered to the mammal daily. Alternatively, the collagen source and/or the cannabinoid can be administered to the mammal intermittently.

The present disclosure is also directed to a nutritional product comprising a cannabinoid and a collagen source, such as a Type II collagen source. In one embodiment, the nutritional product comprises the collagen source and cannabinoid in combination. The nutritional product can comprise a food product or a beverage, such as a pet food. In one aspect, the food product can be a tablet, a capsule, a gummy chewable, an edible film, a liquid suspension, a powder, a syrup, or a lozenge. Additionally, the nutritional product may comprise a collagen source and a cannabinoid in separately deliverable forms. For example, the collagen source may be in any deliverable form such as a powder, a capsule, a food product, a beverage, or the like. The cannabinoid may be in any deliverable form as an oil, a powder, a capsule, a food product, a beverage, or the like and may be delivered in nanoparticulate form or as a spray-dried dispersion.

The present disclosure is also directed to various methods to improve the health of a user in addition to reducing joint discomfort or pain. For example, a product according to the present disclosure may act as an immunomodulatory and/or neuromodulatory agent. For instance, in one embodiment, the composition of the present disclosure can be used to improve immune system health and/or decrease inflammation. In one embodiment, the collagen source and the cannabinoid are administered to a mammal in an amount and ratio sufficient to modulate collagen production and/or joint repair in a mammal. The collagen source and the cannabinoid can be administered to a mammal in amounts and ratios sufficient to modulate cytokine production or other immunoregulatory functions in a mammal. Additionally, the collagen source and cannabinoid can be administered to a mammal in an amount and ratio sufficient to improve neurological function and reduce the sense of nociceptive pain.

DEFINITIONS

The term "therapeutically effective amount" as used herein, with respect to the composition described above, shall mean that dosage, or amount of composition, that provides the specific pharmacological or nutritional response for which the composition is administered or delivered to subjects in need of such treatment. It is emphasized that "therapeutically effective amount", administered to a particular subject in a particular instance, will not always be effective in treating the ailments or otherwise improve health as described herein, even though such dosage is deemed a "therapeutically effective amount" by those skilled in the art. Specific subjects may, in fact, be "refractory" to a "therapeutically effective amount". For example, a refractory subject may have a low bioavailability or genetic variability in a specific receptor, a metabolic pathway, or a response capacity such that clinical efficacy is not obtainable. It is to be further understood that the composition, or supplement, in particular instances, can be measured as oral dosages, or with reference to ingredient levels that can be measured in blood. In other embodiments, dosages can be measured in amounts applied to the skin when the composition is contained with a topical formulation.

The term "delivering" or "administering" as used herein, refers to any route for providing the composition, product, or a nutraceutical, to a subject as accepted as standard by the medical community. For example, the present invention contemplates routes of delivering or administering that include oral ingestion plus any other suitable route of delivery including transdermal, intravenous, intraperitoneal, intramuscular, pulmonary, topical and subcutaneous. Additionally, technology such as nanotechnology, micronization, and spray-dried dispersions may be used to enhance the mode of delivery or administration.

As used herein, "cannabis" may refer to any variety of the Cannabis plant, such as *Cannabis sativa* or *Cannabis indica*, for instance. More particularly, the present disclosure may refer to leaves, stems, seeds and flowers or any other part of the Cannabis plant, as cannabis. Nonetheless, cannabis, as referred to herein, includes cannabis that contains average or high levels of THC and/or CBD (usually known as marijuana), hemp, which may contain low, or very low, levels of THC, industrial hemp, which may refer to a cannabis plant that contains less than 0.3% THC, or combinations thereof.

As used herein, the term "mammal" includes any mammal that may benefit from improved joint health and can include without limitation canine, equine, feline, bovine, ovine, human, or porcine mammals.

"Cannabinoids" are a group of compounds including the endocannabinoids, the phytocannabinoids and those which are neither endocannabinoids or phytocannabinoids, hereafter "syntho-cannabinoids".

"Endocannabinoids" are endogenous cannabinoids, which are high affinity ligands of CB1 and CB2 receptors.

"Phytocannabinoids" are cannabinoids that originate in nature and can be found in the cannabis plant. The phytocannabinoids can be present in an extract including a botanical drug substance, isolated, or reproduced synthetically.

"Syntho-cannabinoids" are those compounds capable of interacting with the cannabinoid receptors (CB1 and/or CB2) but are not found endogenously or in the cannabis plant. Examples include WIN 55212 and rimonabant.

A "synthetic cannabinoid" is one which has been produced by chemical synthesis this term includes modifying an isolated phytocannabinoid, by for example forming a pharmaceutically acceptable salt thereof.

Other features and aspects of the present disclosure are discussed in greater detail below.

DETAILED DESCRIPTION

It is to be understood by one of ordinary skill in the art that the present discussion is a description of exemplary embodiments only and is not intended as limiting the broader aspects of the present disclosure.

In general, the present disclosure is directed to products or compositions, such as nutritional supplements, medicinal and/or food formulations, or beverages for administering to humans and animals that can be used as a daily or periodic supplement or to treat a particular ailment. Of particular advantage is that the composition can be formulated to provide multiple health benefits simultaneously.

In one embodiment, for instance, the composition of the present disclosure is particularly formulated to improve musculoskeletal health, such as joint health. For instance, the product or composition can be used to treat arthritis or non-arthritic joint pain, joint discomfort, or lack of joint flexibility.

In general, the composition of the present disclosure contains a collagen source, such as denatured or undenatured Type II collagen, in combination with a cannabinoid. It is believed that the cannabinoid can work synergistically with the collagen. For example, in one embodiment, the cannabinoid can increase the effectiveness of the collagen and/or reduce pain during the healing process.

Cannabinoids that may be incorporated into the nutritional product of the present disclosure include endocannabinoids, phytocannabinoids and syntho-cannabinoids. In one embodiment, for instance, one or more cannabinoids incorporated into the product include phytocannabinoids that are extracted from plants, such as cannabis. In another embodiment, one or more cannabinoids incorporated into the product are biosynthesized by microbes such as yeast or bacteria.

Cannabis is known to contain over 80 different cannabinoid species. Cannabinoids are chemical compounds that act on the endocannabinoid system. The endocannabinoid system comprises CB1 and CB2 cannabinoid receptors, endogenous cannabinoids (endocannabinoids), and the enzymes that synthesize and degrade endocannabinoids. The CB1 and CB2 receptors are members of the G protein-coupled receptors (GPCRs) family, located in the cellular membrane. CB1 is mainly expressed in the brain and, to a lesser extent, in the liver, kidneys, and lungs. CB2 is expressed mainly in the immune system and the hematopoietic cells. The CB2 receptor is of particular importance because of its promising therapeutic potential without the adverse psychotropic effects associated with the CB1 receptor. For instance, Δ-9-tetrahydrocannibinol (Δ-9-TCH) is the primary psychoactive component of Cannabis and engages the CB1 receptor. In contrast, the CB2 receptor is not associated with these psychotropic effects.

As the CB2 receptor is associated with potential therapeutic effects without the negative psychotropic effects, agonists that target CB2 receptors have been proposed for therapies for the treatment of a range of painful conditions including acute pain, chronic inflammatory pain, and neuropathic pain. CB2 agonists have also been proposed as therapeutics in peripheral disorders that involve inflammation including atherosclerosis and inflammatory bowel disease. Additionally, activation of CB2 receptors may be protective in osteoporosis.

CB2 receptors are class A serpentine receptors primarily coupling to $G_{i/o}$ proteins to modulate an array of signaling pathways: adenylyl cyclase, mitogen-activated protein kinase [MAPK (p44/42 and p38)], c-Jun N-terminal kinase, Akt kinase/protein kinase B, phosphoinositide 3-kinase/Akt nuclear factor κ-light-chain-enhancer of activated B cells, nuclear factor of activated T cells, cAMP response element—binding protein/activating transcription factor, Janus kinase/signal transducer and activator of transcription, sphingomyelinase, and caspase, as well as some potassium and calcium ion channels.

For example, CB2 receptor-mediated pertussis toxin-sensitive Gi/o protein stimulation leads to inhibition of adenylyl cyclase and decreased cAMP levels. MAPKs are enzymes involved in a wide variety of vital signaling cascades in many cellular responses, including cell proliferation, migration, transformation, and cell death. This activation is pertussis toxin-sensitive, indicating involvement of Gi/o protein, but is adenylyl cyclase-independent. p38 MAPK activation by a nonselective CB2 receptor agonist has a proapoptotic effect in the Jurkat human leukemia cell line and cytotoxicity in J774-1 macrophages. This effect is exclusively mediated by CB2 receptors.

CB2 receptors can also modulate the activity of potassium and calcium channels. For example, inhibition of voltage-gated calcium channels in AtT20 cells is mediated by CB2 receptors.

Most G protein-coupled receptors (GPCRs) undergo some degree of internalization following agonist binding. Internalization can play a role in downregulation of the GPCR's ability to signal at the membrane. Additionally, internalized GPCRs can engage novel signaling pathways inaccessible to GPCRs residing on the surface membrane. Thus, internalization of a GPCR in response to a ligand can be considered a form of signaling. CB2 receptors exhibit variable internalization in response to an agonist, with some agonists promoting marked internalization and others being inactive.

CB2 receptors may also recruit arrestin to the plasma membrane. β-Arrestins are multifunctional proteins that downregulate G protein signaling through direct interactions with GPCRs, as well as serving as scaffolds to recruit other signaling complexes to GPCRs.

Functional selectivity is the phenomenon in which different agonists activate distinct (or overlapping) intracellular signaling pathways and is a concept that has important implications for drug development. Functional selectivity, also known as biased agonism or stimulus trafficking, is often noted as different agonists activating signaling pathways with different rank order potencies. A balanced agonist activates all pathways similarly, whereas a biased agonist shows bias toward a subset of pathways. In the most extreme example of functional selectivity, an agonist may maximally activate some signaling pathways and not others.

Theoretically, functional selectivity offers the opportunity to "fine-tune" receptor stimulation. Functional selectivity could facilitate the discovery of agonists that stimulate signaling pathways to elicit desirable therapeutic benefits while avoiding activation of signaling pathways that may lead to undesirable side effects. However, if endogenous ligands are present at significant levels and are balanced agonists, which appears to be the case for endocannabinoids (particularly for 2-arachidonoylglycerol), functionally selective ligands may actually antagonize some signaling pathways activated by endocannabinoids, which could be detrimental. Interestingly, CB2 ligands show significant functional selectivity.

An interesting biologic property of CB2 receptors is their high inducibility, with CB2 mRNA levels often increasing as much as 100-fold following nerve injury or during inflammation. If these increases in mRNA are followed by a corresponding increase in functional receptor protein, and activation of the receptor is therapeutically beneficial, then theoretically this leads to a therapeutically desirable situation in which agonists will stimulate CB2 receptors primarily where their activation will be beneficial. As such, CB2 activation for therapeutic effects is promising.

Cannabinoids, such as CBD, is also an agonist of GPR55, which is a receptor found in the brain and endothelium. The interaction between cannabinoids and the GPR55 receptor may have therapeutic promise in treating Parkinson's disease and pancreatic cell apoptosis. As such, cannabinoids that potentiate both the CB2 and GPR55 receptors have great therapeutic potential.

The CB1 receptor may also be a therapeutic target. For example, the CB1 receptor is activated by endocannabinoids and can serve as a therapeutic product for pain management, inflammation, obesity, and substance abuse disorders.

Although the exact mechanism of action is not known, cannabinoids have anti-inflammatory properties. This is believed to be caused by inhibition of the cycloogygenase-2 (COX-2) enzyme, which catalyzes the production of prostaglandins from arachidonic acid. Endocannabinoids have a similar structure to arachidonic acid and have been suggested to interfere with the inflammatory process. As phytocannabinoids and endocannabinoids also share similarities and both act on the endocannabinoid system, it is believed that phytocannnabinoids may also have anti-inflammatory effects. Furthering this belief, phytocannabinoids have shown to be effective COX-1 and COX-2 inhibitors in vitro.

At least partially due to the anti-inflammatory properties of cannabinoids, they have the ability to reduce pain. In addition, CBD and other cannabinoids are a safe, useful therapeutic for treating osteoarthritis joint neuropathic pain. In accordance with the present disclosure, systematic administration of CBD has been shown to suppress the progression of collagen-induced arthritis by reducing inflammatory cytokine production.

Cannabinoids can also serve as anti-convulsant and neuroprotectant agents. For example, CBD can to regulate $Ca^{2+}$ homeostasis and mediate neuroprotection in neuronal preparations which may explain its identification as an anti-epileptic agent. This action may also offer beneficial protection in disease states that involve hyperexcitability.

CBD can also protect against FCCP toxicity, a mitochondrial uncoupler, causing the collapse of the mitochondrial membrane potential and the release of $Ca^{2+}$ into the cytosol. CBD can protect against other oxidative stress related agents such as hydrogen peroxide and oligomycin. The apparent capacity for CBD to reduce $[Ca^{2+}]_i$ when it is abnormally elevated via interaction with mitochondria-dependent $Ca^{2+}$ regulation may be a valuable property for many disease states associated with $Ca^{2+}$ dysregulation. Moreover, neurodegenerative diseases linked directly to mitochondrial malfunction, such as Huntington's disease and Friedrich's ataxia, may benefit greatly from CBD-based medicines.

According to the present disclosure, any suitable cannabinoid can be incorporated into the nutritional product as long as the cannabinoid can improve at least one health symptom and work in conjunction with a collagen source.

One cannabinoid that can be incorporated into the nutritional product of the present disclosure is cannabidiol (CBD). Cannabidiol is a CB1R antagonist and a CB2R agonist and can beneficially effect brain applications by increasing alertness and lowering anxiety. CBD also has an anti-inflammatory effect and has a potential cardiac protection effect.

Other cannabinoids that are particularly well suited for use in the method and product of the present disclosure include the following:

CBC—cannabichromene
CBN—cannabinol
CBG—cannabigerol
THCv—tetrahydrocannabivarin
CBDv—cannabidivarin
Δ-8-THC—Δ-8-tetrahydrocannabinol
THCA—Δ-9-tetrahydrocannabinolic acid
CBDA—cannabidiolic acid CBD has the following chemical formula: $C_{21}H_{30}O_2$ and the following structure:

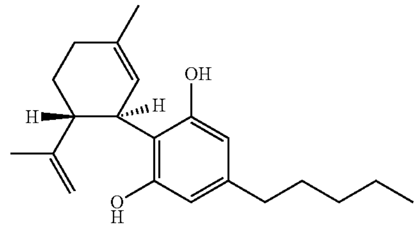 [SMILES: C=C(C)[C@@H]1CCC(C)=C[C@H]1c1c(O)cc(CCCCC)cc1O]

CBD, or cannabidiol, is a non-psychoactive member of the cannabinoids and is one of the most prevalent chemical compounds in the cannabis plant. Found predominantly in the resin glands of the female plant, this compound can stop muscle spasms and epileptic seizures, and can reduce idiopathic anxiety, a prevalent and significantly debilitating aspect of mental illness. It is used to treat nicotine addiction, osteoporosis, diabetes, cancer, obsessive-compulsive disorder, Lupus, Parkinson's disease, and motor disorders, and soothes neuropathic and chronic pain. It has anti-inflammatory, antioxidant, neuroprotectant, anxiolytic, antidepressant, analgesic, anti-tumor, and anti-psychotic effects.

CBC stands for cannabichromene, and has the following chemical formula; $C_{21}H_{30}O_2$ and the following structure:

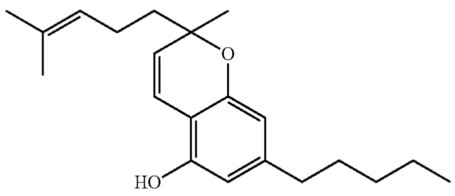 [SMILES: CCCCCc1cc(O)c2c(c1)OC(C)(CCC=C(C)C)C=C2]

Cannabichromene, or CBC, is the third most prevalent cannabinoid in the marijuana plant in general. In some strains CBC is more prevalent than CBD, and like CBD it is non-psychoactive.

CBC is anti-inflammatory. It has anti-tumor effects and shows promise in fighting breast cancer. It may be useful as an antidepressant and may be more powerful than the other cannabinoids in this capacity. CBC shows antiviral and mild antifungal activity. While CBC addresses several other health issues, including inflammation, cancer, depression, and fungal infections, it also increases the number of brain cells and therefore is useful in the treatment of several brain related disorders. CBC promotes neurogenesis in individuals at any age. This not only affects memory and learning but can off-set certain dementias which occur when the brain stops growing new cells. It is likely that CBC can alleviate to some extent certain forms of depression and neuro-degenerative diseases via this particular mechanism of neurogenesis.

CBN stands for cannabinol and has the following chemical formula: $C_{21}H_{26}O_2$ and the following structure:

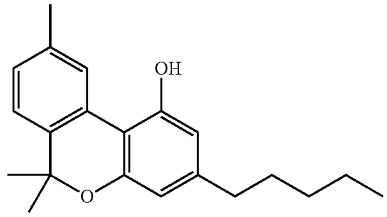 [SMILES: CCCCCc1cc(O)c2c(c1)OC(C)(C)c1ccc(C)cc1-2]

Cannabinol, or CBN, emerges when the dried cannabis flower becomes stale over time. CBN has antibiotic properties, including against methicillin-resistant *Staphylococcus aureus* (MRSA), and also has pain-relieving properties through the release of endorphins. It may delay the onset of, and relieve symptoms of, degenerative motor neural diseases such as amyotrophic lateral sclerosis (ALS) and MS. It works as an appetite stimulant and is more powerful than CBD and CBG in this regard. It has been found to have potent sedative characteristics, making it possibly the most potent single sedative of all the cannabinoids.

CBG stands for cannabigerol, and has the following chemical formula; $C_{21}H_{32}O_2$ and the following structure:

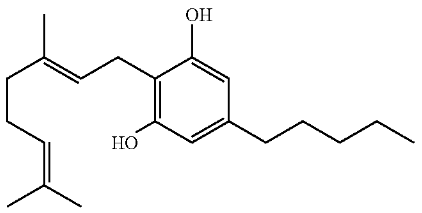 [SMILES: CCCCCc1cc(O)c(C/C=C(\C)CCC=C(C)C)c(O)c1]

CBG, or cannabigerol, is found in cannabis early in the growth cycle. It is non-psychoactive and can also be cultivated in hemp, in which it occurs in greater quantities. CBG has antibiotic properties stronger than CBN and comparable to CBD and is effective against various types of bacteria and fungi. It has therapeutic potential for skin conditions like psoriasis and eczema. CBG is a potent pain reliever.

THCV stands for tetrahydrocannabivarin, and has the following chemical formula: $C_{19}H_{26}O_2$ and the following structure:

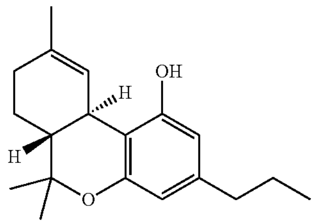 [SMILES: CCCc1cc(O)c2c(c1)OC(C)(C)[C@@H]1CCC(C)=C[C@@H]21]

THCV, or tetrahydrocannabivarin, has medical uses that include antiepileptic, anticonvulsant, and anti-seizure; it promotes weight loss by suppressing the appetite and possibly decreasing body fat and boosting energy metabolism.

CBDV stands for cannabidivarin, and has the following chemical formula: $C_{19}H_{26}O_2$ and the following structure:

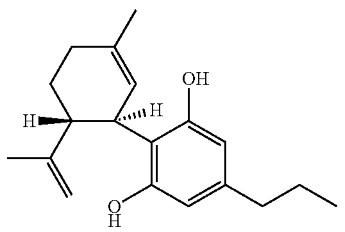 [SMILES: C=C(C)[C@@H]1CCC(C)=C[C@H]1c1c(O)cc(CCC)cc1O]

Cannabidivarin, or CBDV, is a slightly-degraded close relative of CBD. It is used as an anticonvulsant, an antiepileptic, and has antiemetic properties (as well as aiding those with gastrointestinal issues).

Δ-8-THC stands for Δ-8-tetrahydrocannabinol, and has the following chemical formula $C_{21}H_{30}O_2$ and the following structure:

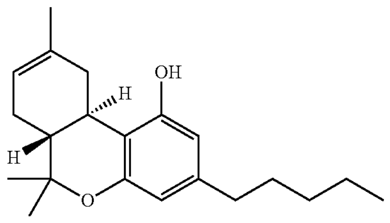 [SMILES: CCCCCc1cc(O)c2c(c1)OC(C)(C)[C@@H]1CC=C(C)C[C@@H]21]

Δ-8-tetrahydrocannabinol is not psychoactive. It has both neuroprotective and anti-anxiety properties, as well as being anti-emetic.

THCA stands for Δ-9-tetrahydrocannabinolic acid, and has the following chemical formula for which is $C_{22}H_{30}O_4$ and the following structure:

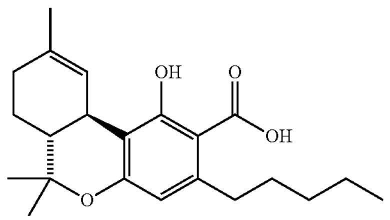 [SMILES: CCCCCc1cc2c(c(O)c1C(=O)O)[C@@H]1C=C(C)CC[C@H]1C(C)(C)O2]

Δ-9-tetrahydrocannabinolic acid, or THCA, is a non-psychoactive compound found in cannabis prior to decarboxylation to the psychoactive version, THC, by application of heat or drying or both. THCA levels are particularly high in the live or freshly harvested plant. THCA shows anti-inflammatory properties and may thus be used in treatment of arthritis and lupus. Its neuroprotective properties may make THCA a candidate for treatment of neurodegenerative diseases; its anti-emetic properties making it a possible treatment for nausea and appetite loss, and its anti-proliferative properties making it a candidate in treatment in certain cancers such as but not limited to prostate cancer.

CBDA stands for cannabidiolic acid, and has the following chemical formula: $C_{22}H_{30}O_4$ and the following structure:

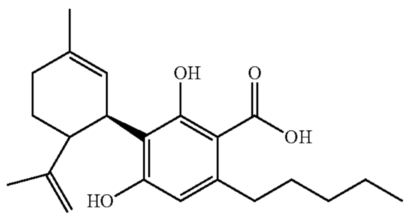 [SMILES: C=C(C)C1CCC(C)=C[C@H]1c1c(O)cc(CCCCC)c(C(=O)O)c1O]

Cannabidiolic acid, or CBDA, has antibacterial, anti-emetic, anti-inflammatory, and cancer cell anti-proliferative effects.

The above cannabinoids can be extracted from plants, such as cannabis, using various methods. For instance, in one embodiment, the above cannabinoids can be extracted from plants in the form of an oil. The extraction process may be performed using a liquid organic solvent such as ethanol or a supercritical fluid such as carbon dioxide to extract the cannabinoids from the fibrous plant material. The solvent may then be removed from the cannabinoid oils using an evaporation or distillation process, leaving a crude cannabinoid oil. The crude cannabinoid oil can optionally be further purified using distillation, chromatography, or the like. Purification can be used to remove any Δ-9-THC or to isolate a particular desired cannabinoid. For example, Δ-9-THC may be removed in order to reduce any psychotropic effects.

The cannabinoid may also be obtained from hemp seed oil. Although hemp seeds do not contain any cannabinoid, their contact with the resin secreted by the epidermal glands located on flowers and leaves and/or a bad selection of the bracts of the perigonium, which have the highest cannabinoid content, can cause the presence of cannabinoids in hemp oil.

Cannabis plants may be selected prior to extraction based on their cannabinoid profile. For example, a cultivar of cannabis may be grown to enhance its proportion of one or more desired cannabinoids to improve the concentration of the one or more cannabinoids in the extract and simplify the purification of the extract. In one embodiment, the cannabinoid is extracted from a cultivar selected for high concentrations of CBD and low concentrations of Δ-9-THC.

In another embodiment, the above cannabinoids as well as other cannabinoids found in smaller amounts in plants are biosynthesized. For example, the cannabinoids may be the product of fermentation using yeast or bacteria. One method of biosynthesizing cannabinoids involves introducing plant genes into yeast and creating an enzymatic network that converts sugars or other starting materials such as fatty acids into cannabinoids. The fermentation products from the yeast can be screened for the best cannabinoid strains while considering productivity and purity, and the most desirable yeast can be isolated and cultivated to create a high-throughput cannabinoid biosynthesis process. Further, the microbes can be genetically manipulated to produce specific cannabinoids and metabolites thereof with specific analgesic effects and other desired benefits.

The biosynthesis process allows for large scale production of cannabinoids that are present in only small amounts in plants as well as cannabinoids not found in plants at all. Additionally, using biosynthesis to produce cannabinoids is a less energy intensive process than growing cannabis plants and extracting the cannabinoids. Further, the purification of biosynthesized cannabinoids is simplified compared to purifying cannabinoids extracted from plants, leading to less contamination in the product.

The cannabinoid may also be a metabolite of any of the cannabinoids described above. For example, the cannabinoid may be a metabolite of CBD such as 2"-OH-7-COOH, 3",4",5"-trinor, CBD-glucuronide, 4"-OH-7-COOH, 2"-OH-7-COOH, 10-OH-7-COOH, 3"-OH-7-COOH, 7-OH-3"-COOH,4",5"-dinor, 7-COOH-8,9-dihydro-8,9-diOH, 1"-OH-7-COOH, 6-OH-4"-COOH,5"-nor, 6-OH-3"-COOH, 4",5"-dinor, or 7-COOH.

The cannabinoid may be administered to the mammal in the form of an oil, powder, or a form leading to increased bioavailability such as micelles, nanoparticles, or a spray-dried dispersion. If the cannabinoid is administered in the form of nanoparticles, the particle size may be from about 10 nm to about 5000 nm, such as from about 50 nm to about 800 nm, such as from about 100 nm to about 350 nm, such as from about 150 nm to about 250 nm.

A micellular emulsion may be formed by mixing a cannabinoid oil with a surfactant, such as a non-ionic surfactant, and then mixing with water. For example, emulsions can be formulated by combining the cannabinoid with a specific mixture of fatty acids, such as oleic, stearic, palmitic, trans-octadecadienoic acid, and arachidic acids. The emulsions can contain other essential oils contained in the hemp plant such as the terpenes myrcene, limonene, alpha & beta-pinene, linalool, b-caryophyllene, caryophyllene oxide, humulene, nerolidol, and phytol. The emulsions can contain a thickening agent, such as beeswax, hard paraffin or cetyl alcohol. Sweetening agents can be added to provide a palatable oral preparation, such as glycerol, sorbitol, or sucrose. These formulations can be preserved by the addition of an antioxidant such as ascorbic acid. The formulations can also be in the form of oil-in-water emulsions. The oily phase can be a vegetable oil or a mineral oil, described above, or a mixture of these. Suitable emulsifying agents include: naturally-occurring gums, such as gum acacia and gum tragacanth; naturally occurring phosphatides, such as soybean lecithin; esters or partial esters derived from fatty acids; and hexitol anhydrides, such as sorbitan monooleate; and condensation products of these partial esters with ethylene oxide, such as polyoxyethylene sorbitan monooleate. The emulsion can also contain sweetening agents and flavoring agents, as in the formulation of syrups and elixirs. Such formulations can further contain a demulcent, a preservative, or a coloring agent.

A spray-dried dispersion may be a single-phase, amorphous molecular dispersion of a cannabinoid in a polymer matrix. It is a solid solution with the cannabinoid molecularly "dissolved" in a solid matrix. Spray-dried dispersions are obtained by dissolving a cannabinoid and polymer in an organic solvent and then spray-drying the solution. The formulation and process conditions are chosen so that the solvent quickly evaporates from the droplets, allowing insufficient time for phase separation or crystallization. In addition to their proven performance in enhancing solubility, spray-dried dispersions have demonstrated long-term stability, facile scale-up and excellent manufacturability. Spray-dried dispersion technology increases the bioavailability of compounds with low solubility in water, such as cannabinoids.

Nanotechnology can also be used to increase the bioavailability of cannabinoids in a variety of ways. For example, nanosized cannabinoid delivery systems may utilize lipid based systems such as liposomes, micelles, nanostructured lipid carriers, pro-nano-lipospheres, lipid-drug conjugate nanoparticles, and nanoemulsions or polymeric-based systems such as poly(lactic-co-glycolic acid) (PGLA) or poly-ε-caprolactone (PCL).

In one embodiment, a liposome formulation may be composed of dipalmitoylphosphatidylcholine and cholesterol, giving liposomes with an average size of from about 300-500 nm. Such a formulation may provide a slow and prolonged release that continues for more than 5 h after administration. Liposomes may also be produced using phosphatidylcholine, phosphatidylethanolamine, phospholipids and other compounds, via film hydration and solvent injection, ultrasonication and calcium alginate encapsulated liposomal suspension.

Micellular preparations may be obtained via solvent injection in water and rapid solvent removal. Micelles may also be obtained by mixing oils, glycerol and non-ionic surfactants. Such micelles may be of a particle size less than 100 nm.

Lipid nanoparticles in a solid particle matrix may be produced from oil/water emulsions by simply replacing the liquid lipid (oil) with a solid lipid, i.e., one that is solid at body temperature. First generation analogues, produced from a solid lipid only, are named solid lipid nanoparticles. The second generation of nanostructured lipid carrier (NLC) particles are produced from a blend of a solid lipid and a liquid lipid, in which the partially crystallized lipid particles, with mean radii≤100 nm, are dispersed in an aqueous phase containing one or more emulsifiers. NLC can be considered suitable carrier systems for cannabinoids because they make use of solid particle matrices instead of fluid matrices, such as emulsions and liposomes, meaning that NLC can better host substances and protect them from degradation. The solid particle matrix is also able to slow the diffusion of cannabinoids from inside the particle to the particle surface. For example, the lipid phase may be composed of a mixture of tristearin and tricaprylin and a nonionic linear copolymer may be added to the aqueous phase to encapsulate the cannabinoid. NLC particles may be used as a dosage form for nasal delivery as well.

Formulations that are based on self-(nano) emulsifying drug delivery technology (SEDDS) may be used as a means of improving the oral bioavailability of cannabinoids. The base formulation, which is an isotropic mixture of a cannabinoid in combination with lipids, surfactants and a co-solvent, has been called a pro-nano-liposphere (PNL) pre-concentrate and is ingested as a soft gelatine capsule. When it reaches the aqueous phase of the gastrointestinal tract, the PNL spontaneously forms a cannabinoid-encapsulated oil/water micro-emulsion with a particle diameter of less than 60 nm. The clinical usefulness of SEDDS, which stems from their ability to increase the solubility and oral bioavailability of cannabinoids, have led to them attracting considerable interest. For example, the formulation may be composed of a cannabinoid in a formulation with polysorbate 20, sorbitan monooleate 80, polyoxyethylene hydrogenated castor oil 40, glyceryl tridecanoate, lecithin and ethyl lactate. This formulation also allows absorption enhancers, such as curcumin, resveratrol and piperine, to be incorporated.

A Lipid Drug Conjugate (LDC) may also be used to deliver the cannabinoid. LDC nanoparticles with approximately 33% loading capacities have been developed. An insoluble cannbinoid-lipid conjugate bulk is prepared either by salt formation with a fatty acid or by covalent linking to esters or ethers. For salt formation, the cannabinoid and fatty acid are dissolved in a suitable solvent. The solvent is then evaporated under reduced pressure. For the covalent linking, the cannbinoid and a fatty alcohol react in the presence of a catalyst and the LDC bulk is then purified by recrystallization. The obtained LDC bulk is then processed with an aqueous surfactant solution to a nanoparticle formulation using high pressure homogenization.

Alternatively, a polymer may be used to deliver the cannabinoid. Responsive polymers, polymer therapeutics and advanced systems for molecular recognition or for the intracellular delivery of novel therapeutics may be advantageously used in conjunction with cannabinoid and collagen product. Polymeric drug delivery systems are able to protect drugs from degradation and control drug release.

The poly(lactic-co-glycolic acid) (PLGA) polymer, for example, may be used for the encapsulation of drugs, as it is mechanically strong, hydrophobic, biocompatible and degrades into toxicologically acceptable products that are eliminated from the body.

PLGA nanoparticles may be loaded with a cannabinoid and may be coated with a variety of agents such as chitosan, PEG-chitosan, Eudragit RS, vitamin E and lecithin. The nanoparticles may have particle sizes of from about 100-1000 nm and high entrapment efficiency values, such as greater than about 80%.

Poly-ε-caprolactone (PCL) is another polymer that may be used. This is a biocompatible, biodegradable, FDA-approved, semi-crystalline aliphatic polyester that degrades slowly. A cannabinoid may be loaded into PCL particles. The PCL particles may be microparticles with a size range of 20-50 μm and a substantially 100% entrapment efficiency.

The cannabinoid may also be administered as micronized particles. For example, a crystalline cannabinoid can readily be granulated and micronized to provide particulate materials and powders for use, e.g., in metered-dose inhalers, or for transdermal, transmucosal, parenteral or oral administration. In particular, formulations for oral administration, e.g. in the form of tablets, pills, or encapsulated particles or suspensions, can be manufactured as immediate-release or controlled-release (e.g. sustained-release) formulations. The cannabinoid microparticles can be formed in a size range consistent with the intended properties such as, e.g. the release rate of the cannabinoid. The cannabinoid of the present disclosure can be micronized to produce particles in a size range of about 0.1 to about 10 microns.

For example, a crystalline cannabinoid can be micronized in a suitable mill, e.g. a jet mill, to produce particles in a size range of about 10 microns. In one approach, the crystalline cannabinoid can be micronized separately from other carriers or excipients included in the formulation. In another approach, one or more of the pharmaceutically-acceptable carriers or excipients included in the product can be combined with the cannabinoid prior to micronization. Such carriers or excipients are known in the art. These include desiccants, diluents, glidants, binders, colorants, preservatives, lubricants, disintegration agents, filling agents, surfactants, buffers and stabilizers. Micronization of the crystalline cannabinoid, optionally in the presence of one or more pharmaceutically-acceptable carriers or excipients can be advantageous in that the particles so produced comprise a uniform distribution and content of the cannabinoid within those particles. It is believed that such particles can provide a more consistent release profile and improved bioavailablity for the finished dosage form into which they are incorporated. For example, such particulate material, e.g. granules, microparticles or nanoparticles comprising the crystalline cannabinoid can be compressed to form tablets or can be distributed to capsules for administration.

The cannabinoid may also be delivered as an extended release capsule. Extended release capsules are enteric-acid resistant and are designed to bypass the stomach acid and only dissolve once they reach the intestine. The capsules may be formed using a pH sensitive polymer so as to dissolve at a minimum pH level. For example, the polymer and capsule may dissolve at a pH of 5.5 or higher, thus preserving the cannabinoid from being destroyed by gastric acids. The extended release capsules can increase bioavailability, for example by up to about 20%. The extended release capsule may begin dissolving after about an hour from being ingested, such as after about 2 hours from being ingested.

In accordance with the present disclosure, the cannabinoid may be delivered separately from the collagen source in any form described above. Alternatively, the cannabinoid may be delivered in any form described above in combination with the collagen source in a single delivery vehicle. For example, the cannabinoid may be present in the form of an oil, powder, nanoparticles, micelles, or a spray-dried dispersion and incorporated into a food product along with the collagen source.

In accordance with the present disclosure, at least one cannabinoid is administered to a mammal in conjunction with a collagen source. It is believed that the cannabinoid can operate synergistically with the collagen source and serve and an adjuvant for the collagen source. For instance, the cannabinoid may increase the percentage of mammals that favorably respond to being administered a collagen source. The cannabinoid may accelerate the onset of action attributed to taking routine dosages of collagen in mammals. In addition, the cannabinoid can provide pain relief and reduce inflammation. Overall, it is believed that the cannabinoid provides faster and more enhanced treatment to the patient when combined with a collagen source.

Collagen is a protein that can be found in muscles, bones, skin, blood vessels, and in other parts of the body. There are various types of collagen which differ in function and form. For instance, Type I collagen, the most abundant collagen, is made of fibers found in tendons, ligaments, organs, and skin. Type II collagen, on the other hand, primarily helps build cartilage, a major structural entity that sits on the surfaces of those bones which comprise articulating joints. Type III collagen is made of fibers and is a major component of the extracellular matrix that makes up organs and skin. Type III collagen also forms blood vessels and tissue within the heart.

Numerous different products, including cosmetic creams and body lotions, contain collagen. Various oral supplements also contain collagen. Collagen production in the body, for instance, tends to slow as a person ages. For this reason, humans consume collagen supplements that reduce the effects of aging by improving the health of skin and hair.

Collagen has also been used as a pet food supplement. For example, collagen can improve general bone and joint heath in animals. In this regard, collagen can help improve the health of an animal suffering from osteoarthritis. Collagen is also used to promote a healthy coat and skin on pets. Finally, collagen is fed to pets and animals in order to help with digestion and to prevent leaky gut.

Collagen has also been found to effectively treat arthritis and other joint pain. For example, U.S. Pat. No. 9,066,926 discloses a method of reducing exercise-induced joint pain in mammals by administering Type II collagen to a mammal. The '926 patent is incorporated herein by reference.

Although collagen can offer various advantages when administered to a human or animal, a need exists for a composition and method that can increase the effectiveness of collagen and/or work in conjunction with collagen to provide synergistic effects.

The collagen present in the product and method of the present disclosure can be any suitable collagen source, particularly a Type II collagen, such as an undenatured Type II collagen. Type II collagen for use in the present disclosure can be obtained from any suitable source. For instance, the collagen can be derived from a variety of mammalian sources, avian sources, or fish species. For instance, the collagen can be obtained from salmon, shark, poultry, eggshells, turkey cartilage, bovine cartilage, and the like. In one embodiment, for instance, the Type II collagen can be obtained as disclosed in U.S. Pat. No. 7,083,820 to Schilling, which is incorporated by reference. For example, undenatured Type II collagen is available commercially as the UC-II® brand from InterHealth Nutraceuticals. The UC-II® brand is a natural ingredient that contains a glycosylated, undenatured Type II collagen derived from chicken sternum. The collagen source can also comprise a hydrolyzed collagen as well as a pure native collagen protein that can be produced via enzyme hydrolysis, or fermentation techniques, or other methods known to those skilled in the art. In one embodiment, the collagen source can be free of any bone or bone material. In other embodiments, the collagen source can be free of any TGF-β, bone morphogenic proteins, or both. In still another embodiment, the collagen source comprises Type II collagen.

In preparing animal tissue for oral administration, in one embodiment, the undenatured Type II collagen-containing tissue can be first dissected free from surrounding tissues and diced or otherwise separated into particles. The particulate, or milled, cartilage can then be sterilized by means that do not affect or denature the structure of most of the Type II collagen in the tissue. This material is finally formed into doses containing therapeutically effective levels of undenatured Type II collagen, said levels being generally in the amount of at least about 0.001 gram and preferably from about 0.001 grams to about 0.5 grams of animal tissue per dose. Because this is a natural product, some variation from sample to sample is to be expected. These variations can be minimized by blending after separation into particles. The blending is aided by analytical techniques that allow the amount of undenatured Type II collagen and other constituents to be measured. These measurements will allow batches to be blended for uniformity.

Hydrolyzed collagen comes from skin, bone, or connective tissue, a known byproduct of the meat industry (gelatin). Breakdown of the type II collagen (e.g., joints) to small peptides is achieved via enzymatic, chemical, or a mix of both of these procedures.

A nutritional product or composition of the present disclosure can be administered in an oral form. The collagen source and the cannabinoid may be administered to a mammal separately or can be administered together, in part or in whole. In one embodiment, for instance, the collagen source can be mixed together with the cannabinoid.

In one embodiment, the nutritional product is formed into a dosage vessel, such as a tablet or capsule that can be taken orally. The nutritional product, for instance, can be manufactured in the form of capsules, tablets, gummy chewables, edible films, lozenges, powders, liquid suspensions, syrups, lipid micelles, spray-dried dispersions, nanoparticles, and the like. The collagen source and the cannabinoid may be combined together within the dosage vessel or can be contained in the dosage vessel and separated from one another. Alternatively, the components of the nutritional product can be administered separately, each of which components can exist in alternative, different forms.

Alternatively, the collagen source and the cannabinoid can be contained in a food product or in a beverage. In one embodiment, for instance, the collagen source and the cannabinoid can be contained in a pet food for consumption by an animal. The pet food, for instance, can be fed to any suitable mammal, such as a canine or a feline. The pet food may comprise from about 5% to about 50% of protein by weight. The protein source may be vegetables such as soybean meal or may be an animal protein such as meat protein. Examples of meat protein include beef, pork, lamb, poultry, fish and the like. The food composition/pet food may further comprise from about 5% to about 40% by weight fat. The fat may comprise animal fats and/or vegetable fats. The food composition may further comprise a carbohydrate. The carbohydrate may be present in an amount greater than about 10% by weight. The carbohydrate may be obtained from grains and cereals. In addition to dogs and cat, the food composition is particularly well suited for administering to horses, cattle, and the like. In one embodiment intended for human consumption, the food product is a protein bar.

The amount of the collagen source and the amount of the cannabinoid in a dose consumed at any given time will vary with the purpose of consumption and the severity of symptoms, as well as the condition, age, weight, medical history, and general physical characteristics of the subject (human or animal) to be treated or supplemented. Consequently, the dosages, frequency, and period of time over which dosages are administered can vary widely. The nutritional product of the present disclosure can be combined with other digestible ingredients, such as those in the form of aqueous dispersions such as milk, or with other protein-rich substances, sugars, and starches. In one embodiment, the nutritional product may be administered directly as a comminuted solid as in an encapsulated comminuted solid, such as a compression and formed pill, as well as a slurry with or without other digestible compositions such as, for example, foodstuffs.

The weight ratio between the collagen source and the cannabinoid administered to the mammal can also vary depending upon many factors. In one aspect, the weight ratio between the collagen and the cannabinoid can be from 1:100 to about 100:1, such as from about 1:50 to about 10:1, such as from about 1:15 to about 1:1. The proportion of cannabinoid used may be on the lower end when methods to improve bioavailability are used such as spray-dried dispersions, lipid micellular technology, nanotechnology, and the like.

In one embodiment, Type II collagen can be administered to a mammal generally in an amount from about 1 μg/kg body weight/day to about 1 g/kg body weight/day, such as from about 250 μg/kg body weight/day to about 1 mg/kg body weight/day. For example, the Type II collagen source can be administered to a mammal in an amount greater than about 5 milligrams per day, such as greater than about 10 milligrams per day, such as greater than about 20 milligrams per day, such as greater than about 30 milligrams per day, such as greater than about 40 milligrams per day, such as greater than about 50 milligrams per day and generally less than about 1,500 milligrams per day, such as less than about 1,000 milligrams per day, such as less than about 800 milligrams per day, such as less than about 600 milligrams per day. In one aspect, the Type II collagen can be an undenatured Type II collagen and can be contained in a dosage vessel in an amount of from about 1 mg to about 50 mg, including all increments of 1 mg therebetween. For instance, an individual dosage can be less than about 40 mg, such as less than about 30 mg, such as less than about 20 mg, such as less than about 15 mg, such as less than about 10 mg, and generally greater than about 2 mg, such as greater than about 3 mg, such as greater than about 5 mg, such as greater than about 8 mg, such as greater than about 10 mg, such as greater than about 15 mg. In this regard, a dosage vessel or a food composition containing the Type II collagen source can contain the collagen source in any of the above identified amounts and fed daily to the mammal.

When denatured or hydrolyzed collagen is present in the composition, the collagen can be administered to a mammal generally in an amount of from about 500 milligrams to about 15,000 milligrams per day or can be contained in a dosage vessel in the above amounts. When undenatured Type II collagen is used to produce the composition, on the other hand, the collagen can be administered to a mammal generally in an amount from about 1 milligram to about 5,000 milligrams per day and/or can be contained in a dosage vessel or a food product in the above amounts.

The cannabinoid can generally be administered to the mammal in an amount of from about 1 μg/kg body weight/day to about 60 mg/kg body weight/day, such as in an amount from about 1 mg/kg body weight/day to about 20 mg/kg body weight/day. For instance, the cannabinoid can be administered to the mammal in an amount greater than about 500 μg per day, such as greater than about 10 milligrams per day, such as greater than about 50 milligrams per day, such as greater than about 75 milligrams per day, such as greater than about 100 milligrams per day. The cannabinoid can be administered to the mammal generally in an amount less than about 6,000 milligrams per day, such as less than about 5,000 milligrams per day, such as less than about 3,000 milligrams per day, such as less than about 2,000 milligrams per day, such as less than about 1,500 milligrams per day, such as less than about 1,000 milligrams per day, such as less than about 800 milligrams per day, such as less than about 500 mg per day, such as less than about 200 mg per day, such as less than about 150 mg per day. For instance, the cannabinoid may be administered in any supplement amount allowed by law. When the cannabinoid is administered to the mammal daily, each dosage vessel or serving portion of a food composition can contain the cannabinoid in any of the above amounts.

Bioavailability is generally low for cannabinoids, particularly in plasma. For example, cannabinoid levels in plasma generally range from about 0.1% to about 13% of the supplemental dose. As these are highly lipophilic compounds, they are likely distributed in the tissues rather than the plasma. Therefore, bioavailability should be addressed at the tissue level, such as the brain or macrophages, rather than the plasma to avoid overdosing.

The composition or product of the present disclosure can be taken periodically depending upon the condition of the user and various characteristics of the user. For instance, the composition can be taken daily or intermittently. In addition, it should be understood that the composition or product may be taken more than once daily.

As described above, in one embodiment, the composition of the present disclosure can be formulated as a nutritional supplement or product that is taken orally. It should be understood, however, that the composition or product of the present disclosure can be administered to a human or animal using any suitable method. In one embodiment, the collagen source can be incorporated into a topical composition that is intended to be applied to the skin of a user while the cannabinoid is administered orally. When formulated as a topical composition, for instance, the collagen source can be blended, or separately delivered, with various ingredients and components. For instance, when formulated as a topical composition, the collagen source can be blended with solvents, surfactants, emulsifiers, consistency factors, conditioners, emollients, skin care ingredients, moisturizers, thickeners, lubricants, preservatives, and various different dermatological ingredients. When applied to the skin of a user, the collagen source can be used to improve skin health and/or can be formulated so as to be absorbed into the body. The cannabinoid may be administered orally, in a transdermal form, or through inhalation.

To further potentiate the effects of the composition or product of the present disclosure, a nutritional supplement may be administered to a mammal in an amount sufficient to modulate the CB1 and/or CB2 receptor. Non-limiting examples of the nutritional supplement include Boswellia extract, probiotics, prebiotics, oligofructose, alpha-tocopheryl phosphate, a protium species, thujone, Epigallocatechin-3-O-gallate, curcumin, yangonin, constituent from *Echinacea* species, and arabinogalactan.

In one embodiment, an arabinogalactan is administered to the mammal. It is believed that the arabinogalactan can serve as a prebiotic leading to an increase of Lactobacillus acidophilus in the gut. The presence of L. acidophilus has shown to lead to the production of more CB2 receptor mRNA than CB1 receptor mRNA. Thus, it may be preferable to administer arabinogalactan to the mammal to increase the interaction between the cannabinoid and the CB2 receptor, while minimizing the interaction between the cannabinoid and the CB1 receptor.

In one embodiment, an oligofructose is administered to the mammal. It is believed that oligofructose acts as a downregulator for the CB1 receptor. Therefore, it may be preferable to administer an oligofructose to the mammal to decrease the interaction between the cannabinoid and CB1 receptors.

In one embodiment, a phosphate derivative of Vitamin E, such as alpha-tocopheryl phosphate, is administered to the mammal. It is believed that a phosphate derivative of Vitamin E modulates synaptic transmissions. In another embodiment, a protium species containing pentacyclic triterpene is administered to the mammal. Pentacyclic triterpene has a high affinity for CB1 and CB2 receptors and can be used to modulate the interactions between the cannabinoid and the cannabinoid receptors.

In one embodiment, thujone and/or Epigallocatechin-3-O-gallate is administered to the mammal. These substances have micromolar affinities for the CB1 receptor and can be used to modulate the interaction between the cannabinoid and the CB1 and, indirectly, the CB2 receptors.

In one embodiment, curcumin is administered to the mammal. Curcumin may elevate endocannabinoid levels and nerve growth factor levels. In another embodiment, yangonin, a kavalactone extracted from kava (Piper Methysticum) is administered to the mammal. Yangonin has an affinity for CB1 receptors.

In one embodiment, a constituent from an *echinacea* species is delivered to the mammal. For example, the constituent may be an alkamide, which binds to CB2 receptors with nanomolar affinity and acts as a CB2 agonist with immunomodulatory effects. In another embodiment, the constituent may be from Echinacea purpurea, which acts as a weak CB1 receptor antagonist.

The composition or product of the present disclosure may also comprise an antioxidant in addition to the cannabinoid and collagen source. While cannabinoids have antioxidant properties themselves, it is believed that the addition of another antioxidant may be further beneficial to a mammal's health and in some instance may modulate cannabinoid receptors. Examples of the antioxidant that may be added to the composition or product include vitamins, stilbenoids, curcumininoids, tannins, flavones, flavonols, flavan-3-ols, flavanones, anthocyanidins, anthocyanins, isoflavones, flavanonols, proanthocyanidins, dihydroxybenzoic acids, carotenoids, and pyridine alkaloids.

For example, in one embodiment the antioxidant comprises one or more antioxidant vitamins, which are desirably selected from the group consisting of vitamin B, vitamin C, and vitamin E and desirably is derived from a food or plant source, for example, green tea, acai, and the like.

In one embodiment, the antioxidant comprises an extract containing one or more stilbenoids, which are desirably selected from the group consisting of resveratrol, piceatannol, pterostilbene, and astringin. In one embodiment the antioxidant comprises one or more curcumininoids, which are desirably selected from the group consisting of curcumin, demethoxycurcumin, and bisdemethoxycurcumin.

In one embodiment, the antioxidant comprises one or more tannins selected from the group consisting of hydrolyzable tannins, gallic acid, gallic acid C1-12 alkyl esters, ethyl gallate, propyl gallate, octyl gallate, dodecyl gallate, theaflavin esters of gallic acid, and condensed tannins (e.g., proanthocyanidins, prodelphinidins, procyanidins, oligomeric proanthocyanidins, leukocyanidins, leucoanthocyanins).

In one embodiment, the antioxidant comprises one or more flavones selected from the group consisting of apigenin, luteolin, tangeritin, chrysin, 6-hydroxyflavone, baicalein, scutellarein, wogonin, and orientin.

In one embodiment, the antioxidant comprises one or more flavonols selected from the group consisting of 3-hydroxyflavone, azaleatin, fisetin, galangin, gossypetin, isorhamnetin, kaempferide, kaempferol, morin, myricetin, natsudaidain, pachypodol, quercetin, rhamnazin, and rhamnetin.

In one embodiment, the antioxidant comprises one or more flavan-3-ols selected from the group consisting of catechin, epicatechin, gallocatechin, epigallocatechin, catechin gallate, epicatechin gallate, epigallocatechin gallate, epiafzelechin, fisetinidol, guibourtinidol, mesquitol, robinetinidol.

In one embodiment, the antioxidant comprises one or more flavanones selected from the group consisting of butin, eriodictyol, hesperetin, hesperidin, homoeriodictyol, isosakuranetin, naringenin, pinocembrin, poncirin, sakuranetin, sakuranin, and sterubin.

In one embodiment, the antioxidant comprises one or more anthocyanins selected from the group consisting of aurantinidin, cyaniding, delphinidin, europinidin, luteolinidin, pelargonidin, malvidin, peonidin, petunidin, rosinidin.

In one embodiment, the antioxidant comprises one or more anthocyanins selected from the group consisting of aurantinidin, cyaniding, delphinidin, europinidin, luteolinidin, pelargonidin, malvidin, peonidin, petunidin, rosinidin.

In one embodiment, the antioxidant comprises one or more pyridine alkaloids selected from the group consisting of trigonelline, arecoline, ricinine, actinidine, gentianine, and gentialutine.

In one embodiment, the antioxidant comprises one or more carotenoids selected from the group consisting of lutein, lycopene, and beta-carotene.

In some embodiments, the antioxidant comprises one or more extracts selected from alfalfa (*medicago sativa*), green tea (*camellia sinesis*), turmeric (*curcuma longa*), edelweiss, eucommia (*eucommia ulmoides*), white tea, black tea, grape (*vitis vinifera*) seed, acai fruit (*euterpe oleracea*), cocoa (*theobroma cacao*), milk thistle, soy, thyme, jiaogulan (*gynostemma pentaphyllum*)(rich in saponins, e.g., gypenosides), rooibos, *Chamomilla Recutita, Scutellaria Baicalensis* Root, carrot, kiwi (*Actinidia chinensis*), *Ampelopsis Grossedentata*, raspberry seed (*Rubus idaeus*), pomegranate seed, elderberry seed, grapefruit seed, black currant seed, cranberry seed (*Vaccinium macrocarpon*), bilberry (*vaccinium myrtillus*) seed, *Pueraria Lobata* Root, Gingko Biloba, Madagascar ambiatry (*Vernonia appendiculata*), Burdock (*arctium lappa*) root, sage, myrtle, hibiscus, Panax ginseng root, olive (*Olea Europaea*) leaf, sweet pea, rosemary, sage, oregano, thyme, black pepper, clove, cinnamon (*Cinnamomum cassia* Presl), coriander, Chinese prickly ash, lemon grass, star anise, mint, sweet basil, bay leaf (*Laurus nobilis* L), and pine bark (*pinus pinaster*) extracts, more preferably eucommia (*eucommia ulmoides*), green tea (*camellia sinesis*), grape (*vitis vinifera*) seed, acai fruit (*euterpe oleracea*), turmeric (*curcuma longa*), and cocoa (*theobroma cacao*) extracts.

In addition to being directed to a composition or a nutritional product, the present disclosure is also directed to a method for administering the nutritional product to a human or animal. For example, in one embodiment, the present disclosure is directed to a method for maintaining joint health and/or treating joint pain including arthritis by administering to a mammal a nutritional product containing undenatured Type II collagen in combination with a cannabinoid. The nutritional product is administered to the mammal in a therapeutically effective amount so as to maintain joint health and/or reduce joint pain or to otherwise treat join pain. In one embodiment, for instance, the reduction in joint pain is evidenced by improvements in range of motion, increased levels of activity, improved knee flexibility, or any activity that depends on having functional knees. In general, as described above, the composition of the present disclosure can be administered orally. In other embodiments, however, the composition can be administered subcutaneously or via a patch.

In other embodiments, the present disclosure is directed to a method of treating a mammal in order to improve immune health, reduce inflammation, or reduce pain. The method includes administering to the mammal the nutritional product as described above in a therapeutically effective amount sufficient to have one of the above effects.

Additionally, the nutritional product as described above may improve health in other ways. For example, cannabinoids have been linked to reducing seizures and anxiety and have been proposed as a treatment for schizophrenia, psychosis, and Parkinson's disease. They have also been found to increase alertness.

CBD is also known to be anxiolytic. For example, CBD treatment reduces anxiety related to public speaking or fearful stimuli in humans. A number of studies have now also shown that CBD reduces the cardiovascular response to anxiety or stressful situations. The potential ability of CBD treatment in humans to reduce the cardiovascular (as well as behavioral) response to stress could have significant effects on the development of atherosclerosis and hypertension, which are known to be accelerated by stress.

Further, CBD is beneficial in preventing ischemia-reperfusion damage in the liver and brain. The cardioprotective effects of CBD may be due to a systemic immunomodulatory effect rather than a direct effect on the heart. CBD may also have additional anti-arrhythmic effects. Furthermore, CBD has significantly reduced cardiac dysfunction in diabetic mice, associated with decreased myocardial inflammation, oxidative stress, nitrative stress and fibrosis, mediated by reduced nuclear factor-κB activation (NFκB), reduced mitogen-activated protein kinase (MAPK) activation and reduced expression of adhesion molecules and tumour necrosis factor (TNF). Other studies have found that the anti-inflammatory effects of CBD via NFκB are not mediated by CB1, CB2 or Abn-CBD receptor activation.

Together, these data suggest that in vivo treatment with CBD has significant cardioprotective effects, which may be through a direct action on the heart or via a general anti-inflammatory, anti-oxidant mechanism.

The present disclosure may be better understood with reference to the following examples.

EXAMPLE 1

Effect of UC-II® Brand Undenatured Type II Collagen and Cannabidiol on Sodium Monoiodoacetate Induced Osteoarthritis(OA) in Rats Male Wistar rats were divided into 6 groups: (i) Control; (ii) MIA-induced rat treated with vehicle; (iii) MIA-induced rats treated with cannabidiol (CBD 1) at a dosage level of 1.62 mg/kg; (IV) MIA-induced rats treated with cannabidiol (CBD 2) at a dosage level of 3.24 mg/kg; (v) MIA-induced rats treated with UC-II® brand Undenatured Type II Collagen at a dosage level of 4 mg/kg combined with CBD 1; and (VI) MIA-induced rats treated with UC-II® brand Undenatured Type II Collagen at a dosage level of 4 mg/kg in combination with CBD 2. OA was induced in male Wistar rats by intra-articular injection of sodium monoiodoacetate (MIA: 1 mg/kg). Treatment was started a week before injection with MIA and lasted 30 days. Biomarker testing was conducted prior to 24 days post MIA. The results of the metabolic marker testing is shown in Table 1, and inflammatory markers are shown in Tables 2 and 3.

TABLE 1

| Markers | Control | MIA | MIA + CBD1 | MIA + CBD2 | MIA + UCII + CBD1 | MIA + UCII + CBD2 | -P- |
|---|---|---|---|---|---|---|---|
| GLU (mg/dL) | 108.43 ± 6.92 | 113.86 ± 10.81 | 112.43 ± 11.52 | 109.86 ± 5.81 | 111.57 ± 7.11 | 112.71 ± 6.05 | 0.872 |
| CR (mg/dL) | 0.44 ± 0.09 | 0.41 ± 0.06 | 0.45 ± 0.11 | 0.45 ± 0.08 | 0.40 ± 0.11 | 0.41 ± 0.10 | 0.910 |
| BUN (mg/dL) | 22.84 ± 2.15 | 23.27 ± 3.66 | 23.57 ± 2.27 | 24.23 ± 1.27 | 23.41 ± 2.98 | 22.03 ± 2.31 | 0.838 |
| TP (g/dL) | 6.84 ± 0.41 | 6.73 ± 0.45 | 6.71 ± 0.17 | 6.87 ± 0.37 | 6.81 ± 0.37 | 6.80 ± 0.47 | 0.816 |
| ALB (g/dL) | 3.63 ± 0.25[ab] | 3.40 ± 0.14[b] | 3.59 ± 0.13[ab] | 3.57 ± 0.14[ab] | 3.64 ± 0.11[a] | 3.71 ± 0.12[a] | 0.012 |
| GLOB (g/dL) | 3.16 ± 0.24[b] | 3.29 ± 0.33[ab] | 3.16 ± 0.05[b] | 3.27 ± 0.23[ab] | 3.37 ± 0.13[ab] | 3.56 ± 0.11[a] | 0.005 |
| ALT (U/L) | 67.86 ± 7.27 | 70.14 ± 5.90 | 69.14 ± 7.63 | 70.29 ± 5.56 | 67.86 ± 9.41 | 67.14 ± 6.18 | 0.950 |
| AST (U/L) | 111.71 ± 12.18 | 115.29 ± 7.50 | 108.43 ± 13.4 | 110.29 ± 12.58 | 109.14 ± 10.54 | 107.71 ± 11.93 | 0.816 |
| ALP (U/L) | 128.43 ± 12.23[a] | 106.43 ± 11.9[b] | 137.14 ± 8.95[a] | 140.43 ± 8.40[a] | 145.29 ± 9.43[a] | 148.29 ± 10.93[a] | 0.001 |

TABLE 1-continued

| Markers | Control | MIA | MIA + CBD1 | MIA + CBD2 | MIA + UCII + CBD1 | MIA + UCII + CBD2 | -P- |
|---|---|---|---|---|---|---|---|
| TBIL (mg/dL) | 0.20 ± 0.01 | 0.19 ± 0.03 | 0.20 ± 0.01 | 0.20 ± 0.01 | 0.21 ± 0.01 | 0.22 ± 0.01 | 0.14 |

GLU: Glucose
CR: Creatine
BUN: Blood Urine Nitrogen
TP: Total Protein
ALB: Albumin
GLOB: Globulin
ALT: Alanine aminotransferase
AST: Aspartate aminotransferase
ALP: Alkaline phosphatase
TBIL: Total Bilirubin

TABLE 2

| | Groups | | | | | | |
|---|---|---|---|---|---|---|---|
| Markers | Control | MIA | MIA + CBD1 | MIA + CBD2 | MIA + UCII + CBD1 | MIA + UCII + CBD2 | --P--* |
| IL-1β (pg/mL) | 13.26 ± 5.36$^{f}$ | 42.40 ± 2.51$^{a}$ | 34.92 ± 2.23$^{bc}$ | 31.94 ± 1.91$^{cd}$ | 27.89 ± 2.37$^{d}$ | 21.59 ± 2.11$^{e}$ | 0.0001 |
| IL-6 (pg/mL) | 6.70 ± 0.48$^{f}$ | 44.06 ± 4.10$^{a}$ | 30.83 ± 2.17$^{c}$ | 28.65 ± 2.17$^{c}$ | 22.93 ± 2.69$^{d}$ | 13.65 ± 2.19$^{e}$ | 0.0001 |
| TNF-α (pg/mL) | 19.01 ± 2.42$^{f}$ | 73.08 ± 5.14$^{a}$ | 46.58 ± 0.87$^{c}$ | 41.97 ± 1.31$^{c}$ | 35.99 ± 2.16$^{d}$ | 26.84 ± 2.49$^{e}$ | 0.0001 |
| COMP (ng/mL) | 5.92 ± 0.62$^{f}$ | 32.2 ± 2.35$^{a}$ | 21.22 ± 1.77$^{c}$ | 16.32 ± 1.91$^{d}$ | 11.02 ± 1.67$^{e}$ | 8.97 ± 0.72$^{e}$ | 0.0001 |
| CRP (mg/L) | 1.56 ± 0.10$^{f}$ | 11.64 ± 1.42$^{a}$ | 6.39 ± 1.06$^{c}$ | 3.95 ± 0.20$^{d}$ | 3.19 ± 0.36$^{de}$ | 2.41 ± 0.43$^{ef}$ | 0.0001 |
| PGE2 (pg/mL) | 248.30 ± 28.87$^{e}$ | 668.96 ± 42.11$^{a}$ | 504.41 ± 37.35$^{bc}$ | 469.24 ± 11.42$^{cd}$ | 422.95 ± 66.07$^{d}$ | 304.01 ± 20.86$^{e}$ | 0.0001 |
| OCN (μg/mL) | 49.73 ± 2.71$^{a}$ | 17.91 ± 1.94$^{g}$ | 28.20 ± 1.74$^{e}$ | 33.35 ± 3.18$^{d}$ | 38.28 ± 1.68$^{c}$ | 42.47 ± 2.19$^{b}$ | 0.0001 |

MIA: Monosodium iodoacetate
TNF-α: tumor necrosis factor α
COMP: cartilage oligomeric matrix protein
PGE2: prostaglandin E2
IL-1β: interleukin-1β
IL-6: interleukin-6
CRP: c-reactive protein
OCN: osteocalcin

TABLE 3

| | Groups | | | | | | |
|---|---|---|---|---|---|---|---|
| Markers | Control | MIA | MIA + CBD1 | MIA + CBD2 | MIA + UCII + CBD1 | MIA + UCII + CBD2 | --P--* |
| MDA (nmol/mL) | 0.57 ± 0.06$^{c}$ | 1.93 ± 0.15$^{a}$ | 1.28 ± 0.08$^{b}$ | 1.24 ± 0.16$^{b}$ | 1.21 ± 0.04$^{b}$ | 1.10 ± 0.06$^{b}$ | 0.0001 |
| SOD (U/mL) | 86.31 ± 6.35$^{a}$ | 37.98 ± 3.19$^{f}$ | 50.00 ± 1.82$^{de}$ | 58.04 ± 2.76$^{c}$ | 54.01 ± 3.03$^{cd}$ | 65.03 ± 3.32$^{b}$ | 0.0001 |
| CAT (U/mL) | 184.25 ± 11.11$^{a}$ | 102.79 ± 8.39$^{e}$ | 125.79 ± 7.41$^{d}$ | 139.36 ± 3.44b$^{c}$ | 128.75 ± 8.93$^{cd}$ | 142.23 ± 4.41$^{b}$ | 0.0001 |
| GSH-Px (U/mL) | 124.69 ± 8.49$^{a}$ | 51.15 ± 7.05$^{e}$ | 75.84 ± 1.15$^{d}$ | 85.31 ± 3.85$^{bc}$ | 78.75 ± 4.56$^{cd}$ | 87.95 ± 6.01$^{b}$ | 0.0001 |

MIA: monosodium iodoacetate;
MDA: malondialdehyde;
SOD: superoxide dismutase;
GSH-Px: glutathione peroxidase;
CAT: catalase.
Statistical comparisons are indicated with different superscript (a-g) in the same row ($P < 0.05$;
*ANOVA and Turkey's post-hoc test).
Mean values of markers are demonstrated with ± standard deviations.

As shown in the tables above, rats treated with a combination of undenatured Type II Collagen and CBD resulted in increased albuim, globulin and ALP-1 levels. Rats treated with a combination of Type II Collagen and CBD also showed a significant reduction in serum inflammation parameters including interleukins, COMP, PGE 2, and CRP. In addition, rats treated with a combination of undenatured Type II Collagen and CBD also showed a decrease in oxidated stress markers such as MDA and a significant increase in antioxidant enzymes. Based on the above, there is clear synergy when the collagen source was combined with the CBD.

Radiographic images of the joints of the test animals were also taken. Knee swelling and knee joint diameter both decreased.

EXAMPLE 2

Effect of UC-II® Brand Undenatured Type II Collagen and Cannabigerol on Sodium Monoiodoacetate Induced Osteoarthritis(OA) in Rats Example 1 was repeated except female rats were treated and cannabidiol was replaced with cannabigerol (CBG). The dosage levels were the same. Tables 4, 5 and 6 below provide the results.

TABLE 4

| | Control | MIA | MIA + CBGI | MIA + CBGII | MIA + UCII + CBGI | MIA + UCII + CBGII | -P- |
|---|---|---|---|---|---|---|---|
| Glucose, mg/dL | 113.43 ± $3.87^{ab}$ | 118.86 ± $4.34^{a}$ | 114.14 ± $3.63^{ab}$ | 112.43 ± $2.99^{ab}$ | 109.29 ± $4.23^{b}$ | 109.29 ± $5.38^{b}$ | 0.003 |
| Creatinine, mg/dL | 0.43 ± 0.07 | 0.39 ± 0.05 | 0.45 ± 0.08 | 0.43 ± 0.07 | 0.44 ± 0.14 | 0.42 ± 0.08 | 0.892 |
| BUN, mg/dL | 20.89 ± 3.77 | 20.46 ± 2.93 | 21.01 ± 1.61 | 22.29 ± 1.52 | 19.03 ± 1.95 | 19.20 ± 2.54 | 0.346 |
| TP, g/dL | 7.16 ± 0.40 | 7.01 ± 0.24 | 6.90 ± 0.38 | 7.34 ± 0.47 | 7.43 ± 0.17 | 7.27 ± 0.38 | 0.59 |
| ALB, g/dL | 3.71 ± $0.13^{abc}$ | 3.64 ± $0.08^{bc}$ | 3.54 ± $0.18^{b}$ | 3.77 ± $0.08^{ab}$ | 3.79 ± $0.11^{ab}$ | 3.87 ± $0.19^{a}$ | 0.001 |
| GLOB, g/dL | 3.50 ± 0.37 | 3.36 ± 0.21 | 3.31 ± 0.25 | 3.57 ± 0.43 | 3.64 ± 0.28 | 3.43 ± 0.25 | 0.299 |
| ALT, U/L | 75.43 ± 10.67 | 76.57 ± 5.19 | 73.43 ± 5.41 | 77.00 ± 10.05 | 69.57 ± 7.68 | 78.29 ± 10.45 | 0.194 |
| AST, U/L | 105.00 ± 13.58 | 110.29 ± 13.07 | 104.14 ± 6.20 | 103.29 ± 15.70 | 104.43 ± 16.86 | 107.14 ± 8.34 | 0.926 |
| ALP, U/L | 156.14 ± 32.66 | 152.86 ± 19.51 | 162.71 ± 19.49 | 157.71 ± 19.53 | 144.86 ± 25.14 | 167.86 ± 34.97 | 0.728 |
| TBIL, mg/dL | 0.21 ± 0.01 | 0.19 ± 0.01 | 0.19 ± 0.02 | 0.22 ± 0.01 | 0.20 ± 0.02 | 0.19 ± 0.01 | 0.10 |

MIA: monosodium iodoacetate;
BUN: Blood urea nitrogen;
TP: Total protein;
ALB: Albumin;
GLOB: Globulin;
ALT: Alanine aminotransferase;
AST: Aspartate aminotransferase;
ALP: Alkaline phosphatase;
TBIL: Total Bilirubin.
Statistical comparisons are indicated with different superscript (a-c) in the same row ($P < 0.05$;
*ANOVA and Turkey's post-hoc test).
Mean values of items are demonstrated with ± standard deviations.

TABLE 5

| Item | Groups | | | | | | --P--* |
|---|---|---|---|---|---|---|---|
| | Control | MIA | MIA + CBGI | MIA + CBGII | MIA + UCII + CBGI | MIA + UCII + CBGII | |
| TNF-α, pg/mL | 25.55 ± $3.83^{e}$ | 78.84 ± $6.10^{a}$ | 56.95 ± $5.61^{b}$ | 54.32 ± $5.01^{b}$ | 43.17 ± $4.25^{c}$ | 34.69 ± $3.28^{d}$ | 0.0001 |
| IL-1β, pg/mL | 15.96 ± $2.28^{d}$ | 41.41 ± $4.02^{a}$ | 35.08 ± $3.41^{b}$ | 34.05 ± $2.80^{b}$ | 25.09 ± $3.42^{c}$ | 21.51 ± $3.48^{c}$ | 0.0001 |
| IL-6, pg/mL | 7.13 ± $0.93^{e}$ | 39.40 ± $3.14^{a}$ | 33.14 ± $4.07^{b}$ | 32.41 ± $3.81^{b}$ | 23.88 ± $3.83^{c}$ | 16.96 ± $2.89^{d}$ | 0.0001 |
| IL-10, pg/mL | 75.32 ± $6.19^{a}$ | 32.59 ± $4.75^{e}$ | 47.42 ± $5.77^{d}$ | 46.17 ± $4.91^{d}$ | 56.84 ± $2.65^{c}$ | 64.53 ± $3.02^{b}$ | 0.0001 |
| COMP, ng/mL | 7.34 ± $1.00^{d}$ | 28.67 ± $2.70^{a}$ | 21.68 ± $2.13^{b}$ | 20.42 ± $2.16^{b}$ | 13.85 ± $1.26^{c}$ | 10.25 ± $1.13^{d}$ | 0.0001 |
| CRP, mg/L | 1.90 ± $0.14^{f}$ | 9.90 ± $0.99^{a}$ | 7.04 ± $0.85^{b}$ | 6.45 ± $0.82^{bc}$ | 4.31 ± $0.57^{de}$ | 3.22 ± $0.69^{e}$ | 0.0001 |
| PGE2, pg/mL | 233.43 ± $15.37^{e}$ | 633.29 ± $39.09^{a}$ | 483 ± $36.86^{b}$ | 473.71 ± $40.89^{b}$ | 350.14 ± $35.96^{c}$ | 287.57 ± $13.51^{d}$ | 0.0001 |

TABLE 5-continued

| | Groups | | | | | | |
|---|---|---|---|---|---|---|---|
| Item | Control | MIA | MIA + CBGI | MIA + CBGII | MIA + UCII + CBGI | MIA + UCII + CBGII | --P--* |
| Osteocalcin, μg/mL | 44.94 ± 2.72[a] | 25.25 ± 2.57[f] | 28.15 ± 1.34[ef] | 30.82 ± 1.35[de] | 36.89 ± 2.18[c] | 40.85 ± 2.16[b] | 0.0001 |

MIA: monosodium iodoacetate;
TNF-α: tumor necrosis factor α;
IL-1β: interleukin-1β;
IL-6: interleukin-6;
IL-10: interleukin-10;
COMP: cartilage oligometrix matrix protein;
CRP: c-reactive protein;
PGE2: prostaglandin E2.
Statistical comparisons are indicated with different superscript (a-f) in the same row ($P < 0.05$;
*ANOVA and Turkey's post-hoc test).
Mean values of items are demonstrated with ± standard deviations.

TABLE 6

| | Groups | | | | | | |
|---|---|---|---|---|---|---|---|
| Items | Control | MIA | MIA + CBGI | MIA + CBGII | MIA + UCII + CBGI | MIA + UCII + CBGII | --P--* |
| MDA, nmol/mL | 0.49 ± 0.06[c] | 1.89 ± 0.07[a] | 1.57 ± 0.07[b] | 1.60 ± 0.07[b] | 1.56 ± 0.09[b] | 1.51 ± 0.07[b] | 0.0001 |
| SOD, U/mL | 82.86 ± 5.18[a] | 38.99 ± 5.63[d] | 49.13 ± 5.76[bc] | 51.13 ± 3.75[bc] | 46.27 ± 6.07[cd] | 55.70 ± 4.23[b] | 0.0001 |
| CAT, U/mL | 173.66 ± 6.45[a] | 107.90 ± 5.81[d] | 136.44 ± 4.10[bc] | 138.82 ± 2.71[b] | 128.78 ± 7.78[c] | 142.91 ± 7.55[b] | 0.0001 |
| GSH-Px, U/mL | 117.95 ± 5.61[a] | 52.65 ± 5.30[d] | 75.87 ± 4.87[bc] | 77.29 ± 5.83[b] | 72.43 ± 4.34[c] | 78.67 ± 7.97[b] | 0.0001 |

MIA: monosodium iodoacetate;
MDA: malondialdehyde;
SOD: superoxide dismutase;
GSH-Px: glutathione peroxidase;
CAT: catalase.
Statistical comparisons are indicated with different superscript (a-e) in the same row ($P < 0.05$;
*ANOVA and Turkey's post-hoc test).
Mean values of items are demonstrated with ± standard deviations.

As shown above, the use of CBG provided similar results in comparison to use of CDB.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only and is not intended to limit the invention so further described in such appended claims.

What is claimed:

1. A nutritional product comprising a Type II collagen source comprising an undenatured Type II collagen, and a collagen adjuvant comprising a cannabinoid, wherein the cannabinoid comprises cannabigerol or cannabidiol, wherein the weight ratio between the Type II collagen source and the cannabinoid is from 1:1 to about 100:1.

2. The nutritional product as defined in claim 1, further comprising an antioxidant.

3. The nutritional product as defined in claim 1, wherein the Type II collagen source and the collagen adjuvant have been blended together or wherein the Type II collagen source and the collagen adjuvant are not blended together.

4. The nutritional product as defined in claim 1, wherein the Type II collagen source further comprises denatured Type II collagen, hydrolyzed Type II collagen, or a bioactive peptide derived from Type II collagen.

5. The nutritional product as defined in claim 1, wherein the nutritional product comprises a food product, the food product comprising a tablet, a capsule, a gummy chewable, an edible film, a liquid suspension, a powder, a syrup, a lozenge, a beadlet, a nanoparticle, a micellular emulsion, or a spray-dried dispersion.

6. The nutritional product as defined in claim 1, wherein the cannabinoid further comprises cannabichromene, cannabinol, tetrahydrocannabivarin, cannabidivarin, cannabidiolic acid, or a mixture thereof.

7. The nutritional product as defined in claim 1, wherein the nutritional product is a beverage, wherein the beverage comprises a liquid suspension, a syrup, a beadlet, a nanoparticle, a micellular emulsion, or a spray-dried dispersion.

8. The nutritional product as defined in claim 1, wherein the nutritional product is a pet food.

* * * * *